(12) United States Patent
Canady et al.

(10) Patent No.: US 11,612,425 B2
(45) Date of Patent: Mar. 28, 2023

(54) CONFIGURABLE ELECTROSURGICAL GENERATOR HOUSING

(71) Applicant: US Patent Innovations, LLC, Takoma Park, MD (US)

(72) Inventors: Jerome Canady, Lakeland, FL (US); Feng Yan, Fairfax, VA (US); Taisen Zhuang, Rockville, MD (US); Aditya Shanghavi, Silver Spring, VA (US); Laxmi Ray, Silver Spring, VA (US); Buddika Sumanasena, Silver Spring, VA (US); Evgueni Sokolovski, Herndon, VA (US)

(73) Assignee: US Patent Innovations, LLC, Takoma Park, MD (US)

(*) Notice: Subject to any disclaimer, the term of this patent is extended or adjusted under 35 U.S.C. 154(b) by 0 days.

(21) Appl. No.: 17/601,551

(22) PCT Filed: Apr. 10, 2020

(86) PCT No.: PCT/US2020/027686
§ 371 (c)(1),
(2) Date: Oct. 5, 2021

(87) PCT Pub. No.: WO2020/210636
PCT Pub. Date: Oct. 15, 2020

(65) Prior Publication Data
US 2022/0192727 A1    Jun. 23, 2022

Related U.S. Application Data

(60) Provisional application No. 62/832,001, filed on Apr. 10, 2019.

(51) Int. Cl.
*A61B 18/04* (2006.01)
*A61B 18/12* (2006.01)
*A61B 18/00* (2006.01)

(52) U.S. Cl.
CPC ........ *A61B 18/1206* (2013.01); *A61B 18/042* (2013.01); *A61B 2018/00178* (2013.01); *H01R 2201/12* (2013.01)

(58) Field of Classification Search
CPC .............. A61B 18/042; A61B 18/1206; A61B 2018/00178; H01R 2201/12
See application file for complete search history.

(56) References Cited

U.S. PATENT DOCUMENTS

| 4,040,426 A | 8/1977 | Morrison |
| 4,429,694 A | 2/1984 | McGreevy |

(Continued)

FOREIGN PATENT DOCUMENTS

| WO | 02/085230 A2 | 10/2002 |
| WO | 2018/191265 A1 | 10/2018 |

*Primary Examiner* — George Manuel
(74) *Attorney, Agent, or Firm* — 24IP Law Group USA, PLLC; Timothy R DeWitt

(57) ABSTRACT

A configurable electrosurgical generator front panel. The configurable electrosurgical generator front panel has a front panel frame, a display screen or tablet computing device, and a plurality of connectors for connecting accessories to the front panel frame. The front panel in the front panel assembly provides a novel structure for inserting a screen or tablet device into the front panel frame and securing it in place.

4 Claims, 12 Drawing Sheets

(56) References Cited

U.S. PATENT DOCUMENTS

| | | | |
|---|---|---|---|
| 4,781,175 A | 11/1988 | Bertrand et al. | |
| 5,207,675 A | 5/1993 | Canady | |
| 2003/0142080 A1* | 7/2003 | Uhl | G06F 1/181 345/173 |
| 2004/0097912 A1 | 5/2004 | Gonnering | |
| 2005/0113818 A1 | 5/2005 | Sartor et al. | |
| 2009/0248022 A1* | 10/2009 | Falkenstein | A61B 18/16 606/51 |
| 2013/0296846 A1 | 11/2013 | Canady et al. | |
| 2014/0378892 A1 | 12/2014 | Guron et al. | |
| 2015/0229083 A1 | 8/2015 | Bopp | |
| 2017/0312004 A1 | 2/2017 | Allen et al. | |

* cited by examiner

CONFIGURABLE ELECTROSURGICAL GENERATOR HOUSING

CROSS-REFERENCE TO RELATED APPLICATIONS

The present application claims the benefit of the filing date of U.S. Provisional Patent Application Ser. No. 62/832,001 filed by the present inventors on Apr. 10, 2019.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to gas-enhanced electrosurgical systems, and more particularly, to a front panel assembly for an electrosurgical generator.

Brief Description of the Related Art

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect, and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in U.S. Patent Application Publication No. 2013/0296846, which disclosed a system for simultaneously cutting and coagulating tissue. Another system, referred to as a "cold atmospheric plasma" system, is disclosed in U.S. Patent Application Publication No. 2014/0378892.

A gas-enhanced electrosurgical generator is disclosed in WO 2018/191265 entitled "Electrosurgical Gas control Module." The gas-enhanced generator has a housing made of a sturdy material such as plastic or metal similar to materials used for housings of conventional electrosurgical generators. The housing has a removable cover. The housing and cover have means, such as screws, tongue and groove, or other structure for removably securing the cover to the housing. The cover may comprise just the top of the housing or multiple sides, such as the top, right side, and left side, of the housing. The housing may have a plurality of feet or legs attached to the bottom of the housing. The bottom of the housing may have a plurality of vents 118 for venting from the interior of the gas-enhanced generator. On the face of the housing there is a touch-screen display and a plurality of connectors for connecting various accessories to the generator, such as an argon plasma probe, a hybrid plasma probe, a cold atmospheric plasma probe, or any other electrosurgical attachment. There is a gas connector for connecting, for example, a $CO_2$ supply for insufflating an abdomen. The face of the housing is at an angle other than 90 degrees with respect to the top and bottom of the housing to provide for easier viewing and use of the touch screen display by a user. A power module and one or more of the gas control modules may be mounted within the gas-enhanced electrosurgical generator. A gas pressure control system for controlling a plurality of gas control modules is within the gas-enhanced electrosurgical generator

SUMMARY OF THE INVENTION

In a preferred embodiment, the present invention is an electrosurgical generator housing. The generator housing has a configurable front panel with a body having a front face, a top, a bottom, a right and a left side, wherein the front face has an opening for receiving a touchscreen display, the opening for receiving a display being at an angle of less than 90 degrees relative to the bottom of the body. The configurable front panel further has a plurality of docks in the front face, each dock being configured to receive an accessory plug module. The front panel may have a plug module in each of the docks in the front face. Each plug module may an alignment groove on one or both outer sides and at least one of the docks has a corresponding alignment ridge or ridges on its interior sides. The plug modules may have a fluid connector and an electrical connector or just a fluid connector or just an electrical connector. One or more of the plug modules may be a blank plug module having no connectors.

The configurable front panel further may have a slot for receiving a printed circuit board and a shield between the slot for receiving a printed circuit board and the plurality of docks. A printed circuit board may be secured in the slot of receiving a printed circuit board.

The gas-enhanced electrosurgical generator housing further may have a base, a back and a cover, wherein the base, back and cover form a compartment and wherein the base has a support structure for securing a gas module and a power module within the compartment. Still further, there may be a shield between the front panel and the compartment.

The front panel provides structure for placing the display/tablet/user interface in the frame without falling out. The configurable front panel further provides a new arrangement for how different plugs fit in the panel. Still further, the present invention decreases electromagnetic interference (EMI).

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
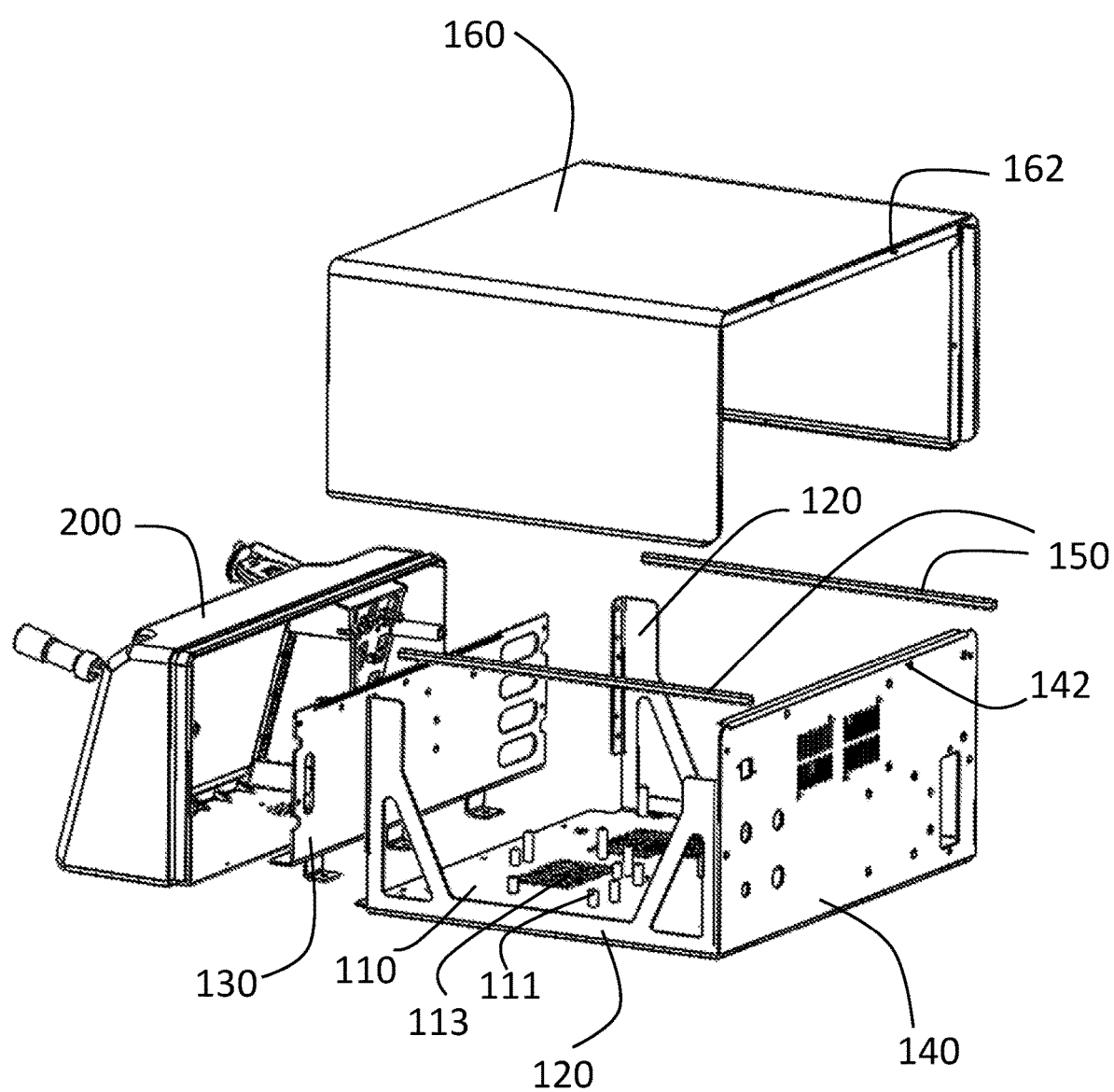
FIG. 1 is an assembly view of an electrosurgical generator housing in accordance with a preferred embodiment of the present invention.
Figure 2A:
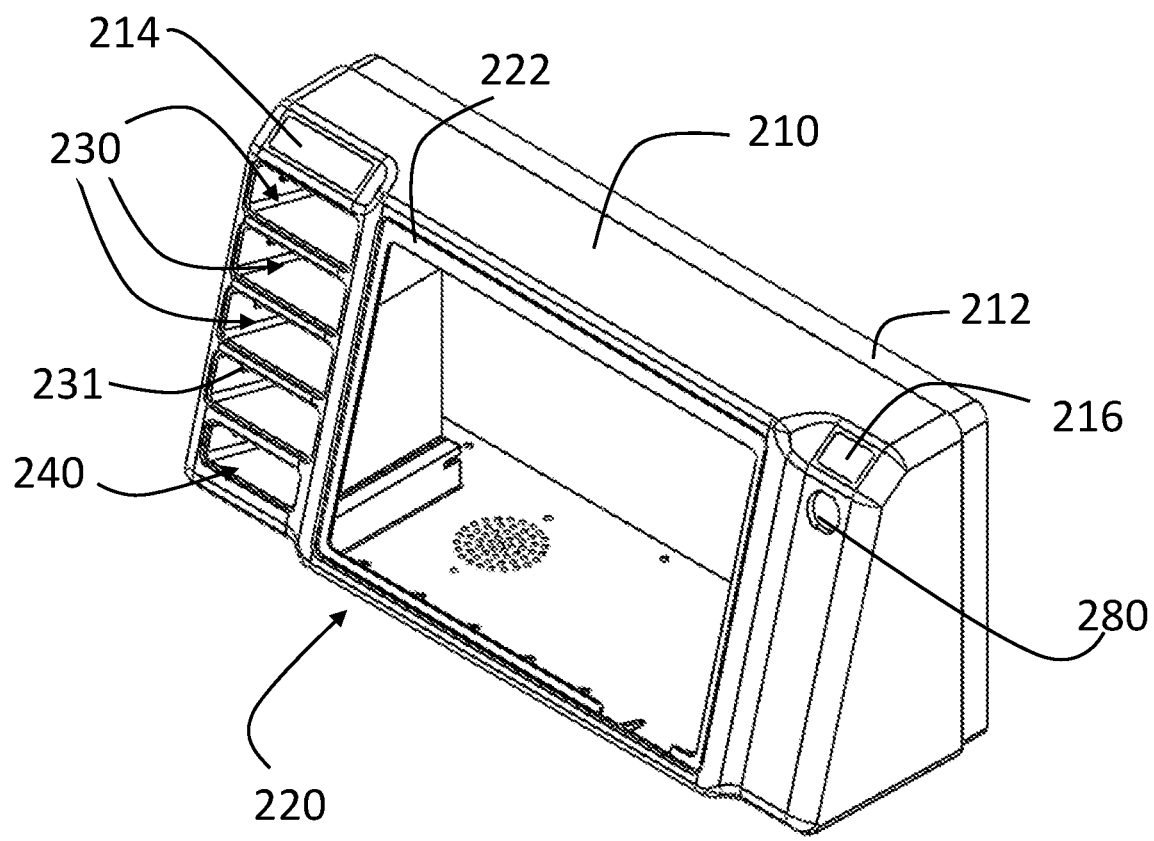
FIG. 2A is a front elevation view of an electrosurgical generator front panel frame in accordance with a preferred embodiment of the present invention.
Figure 2B:
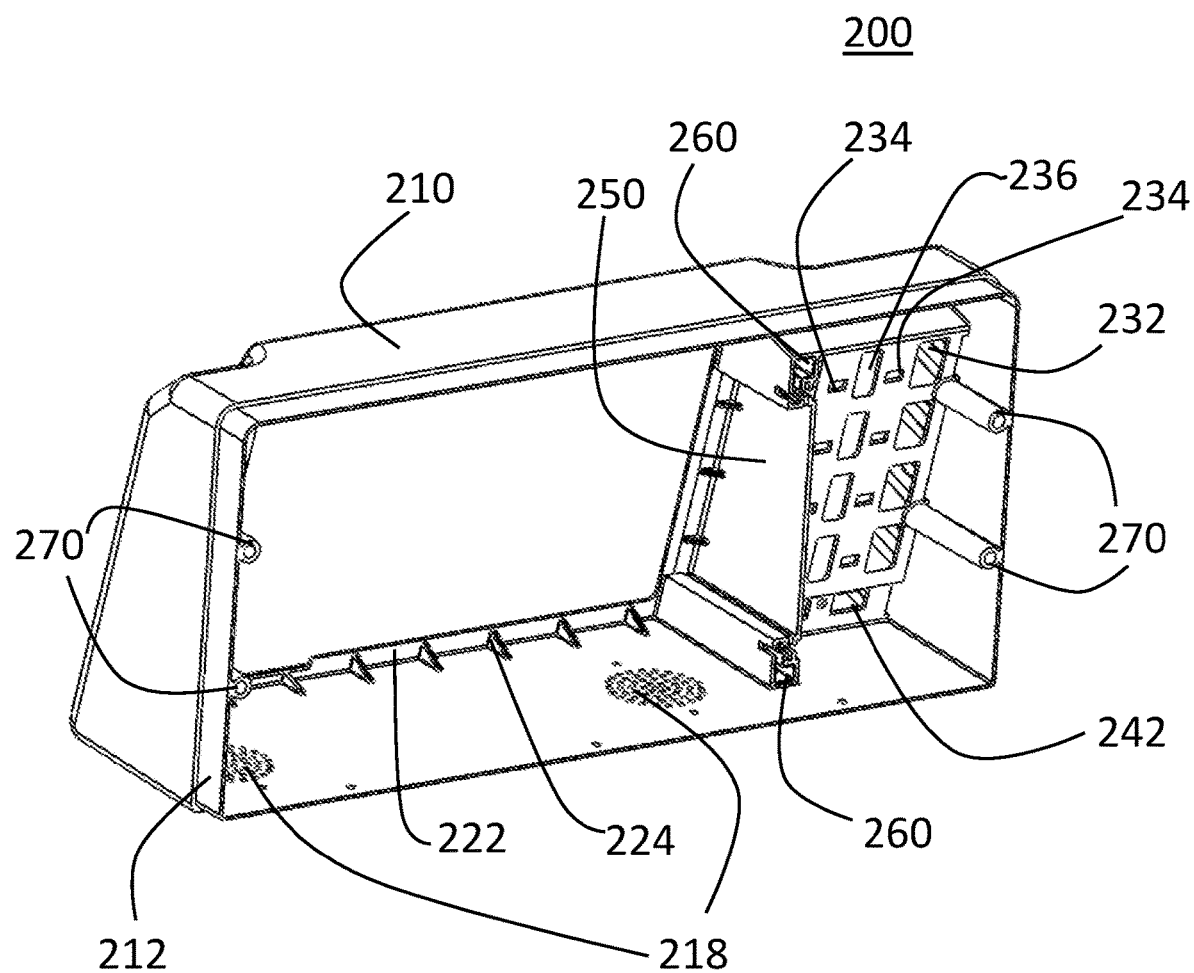
FIG. 2B is a rear elevation view of an electrosurgical generator front panel frame in accordance with a preferred embodiment of the present invention.
Figure 2C:
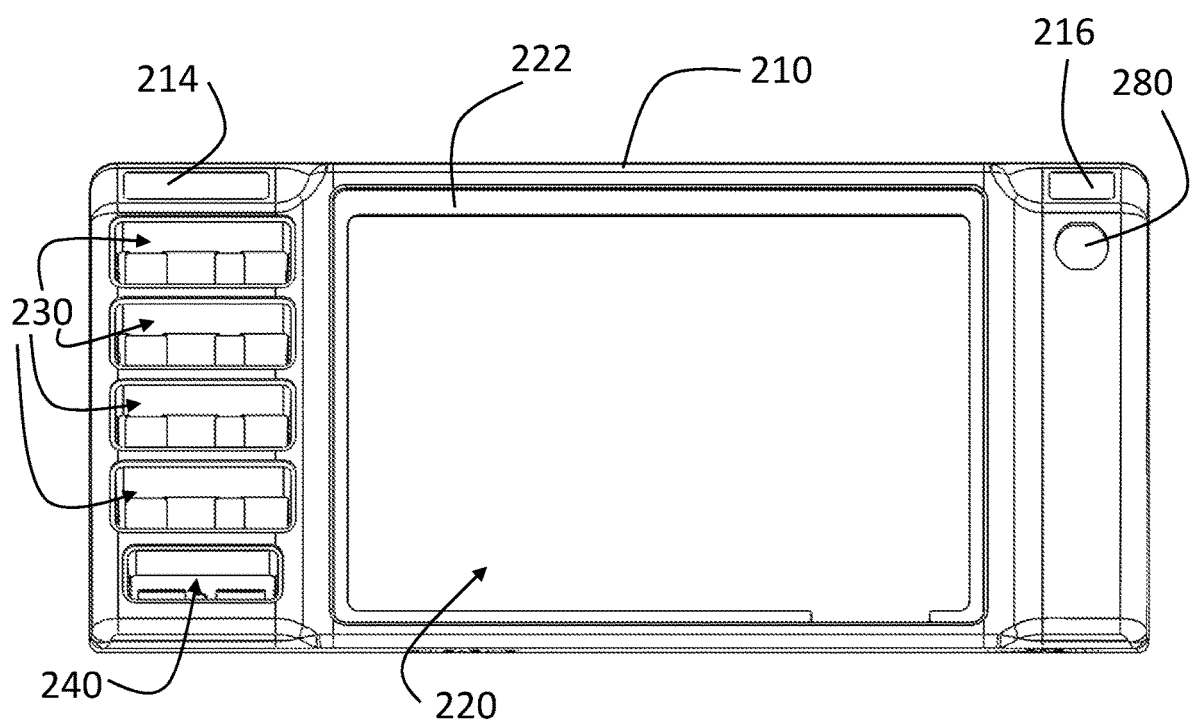
FIG. 2C is a front view of an electrosurgical generator front panel frame in accordance with a preferred embodiment of the present invention.
Figure 2D:
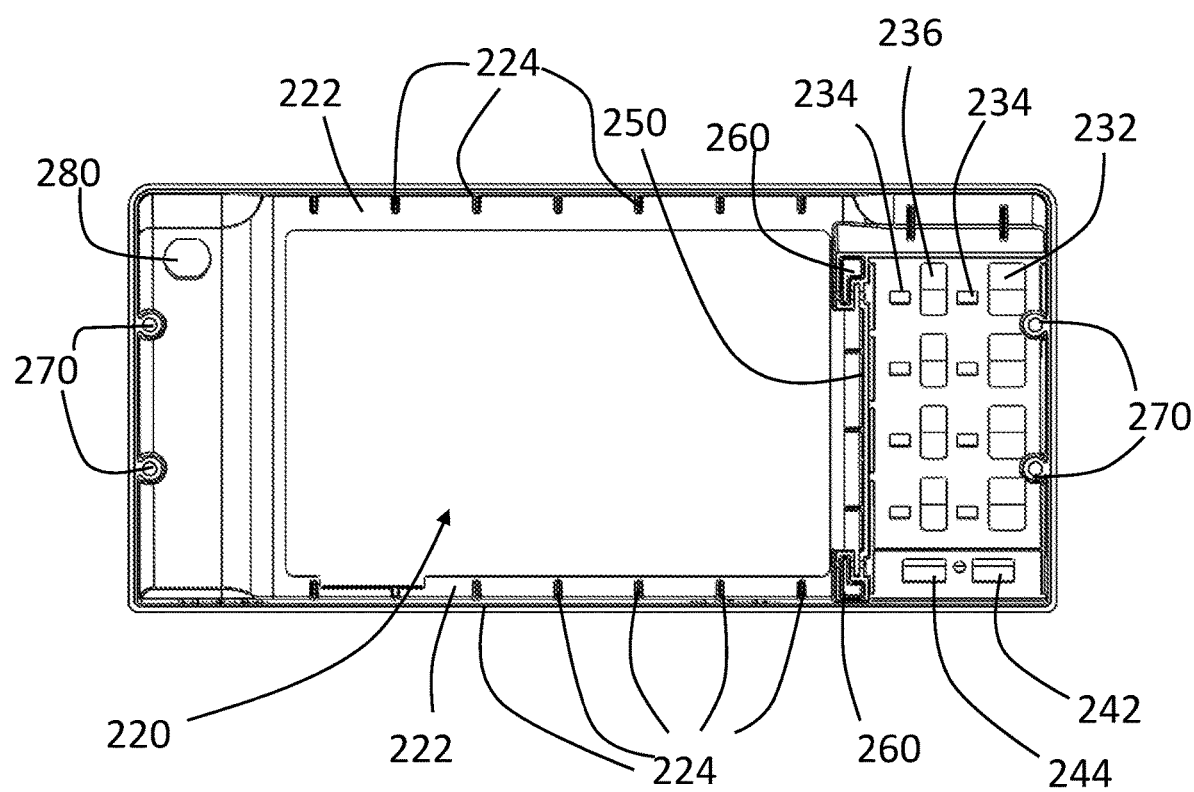
FIG. 2D is a rear view of an electrosurgical generator front panel frame in accordance with a preferred embodiment of the present invention.
Figure 2E:
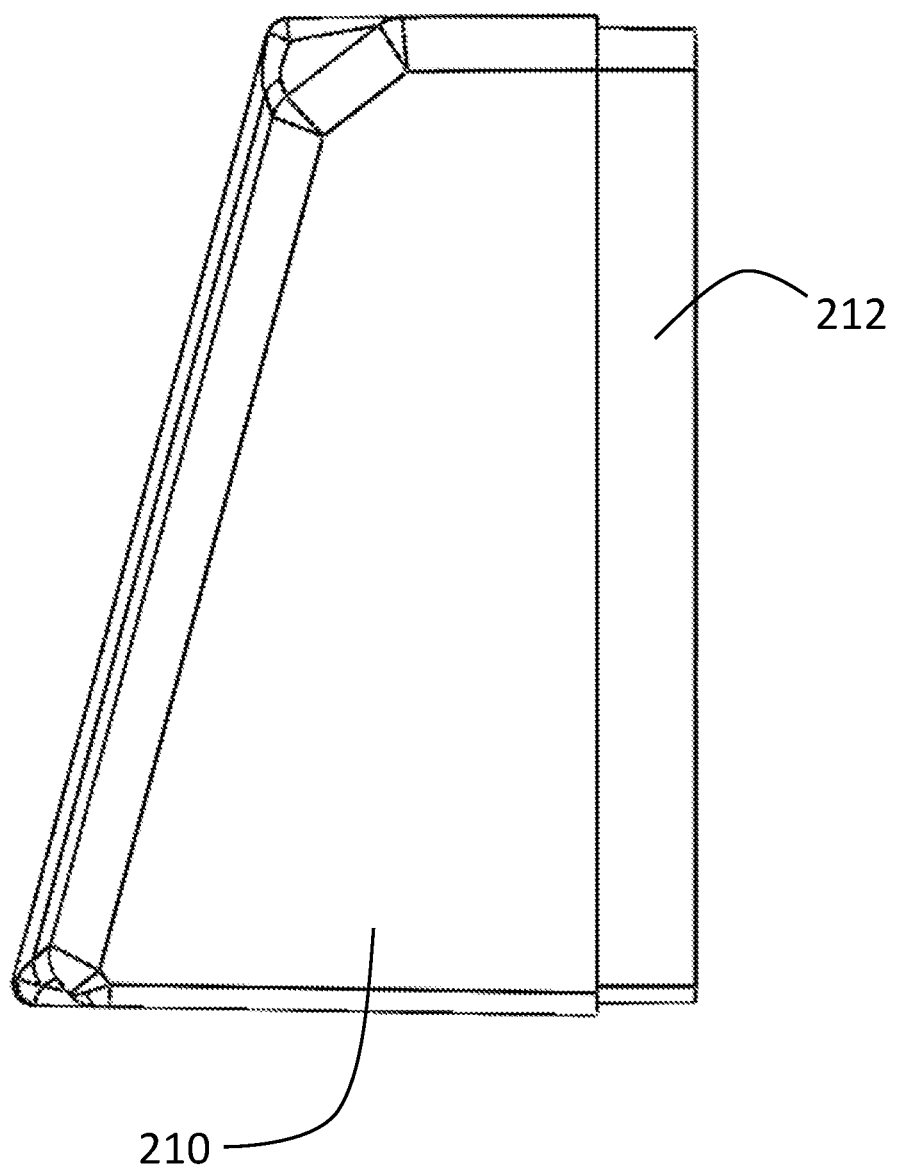
FIG. 2E is a right side view of an electrosurgical generator front panel frame in accordance with a preferred embodiment of the present invention.
Figure 2F:
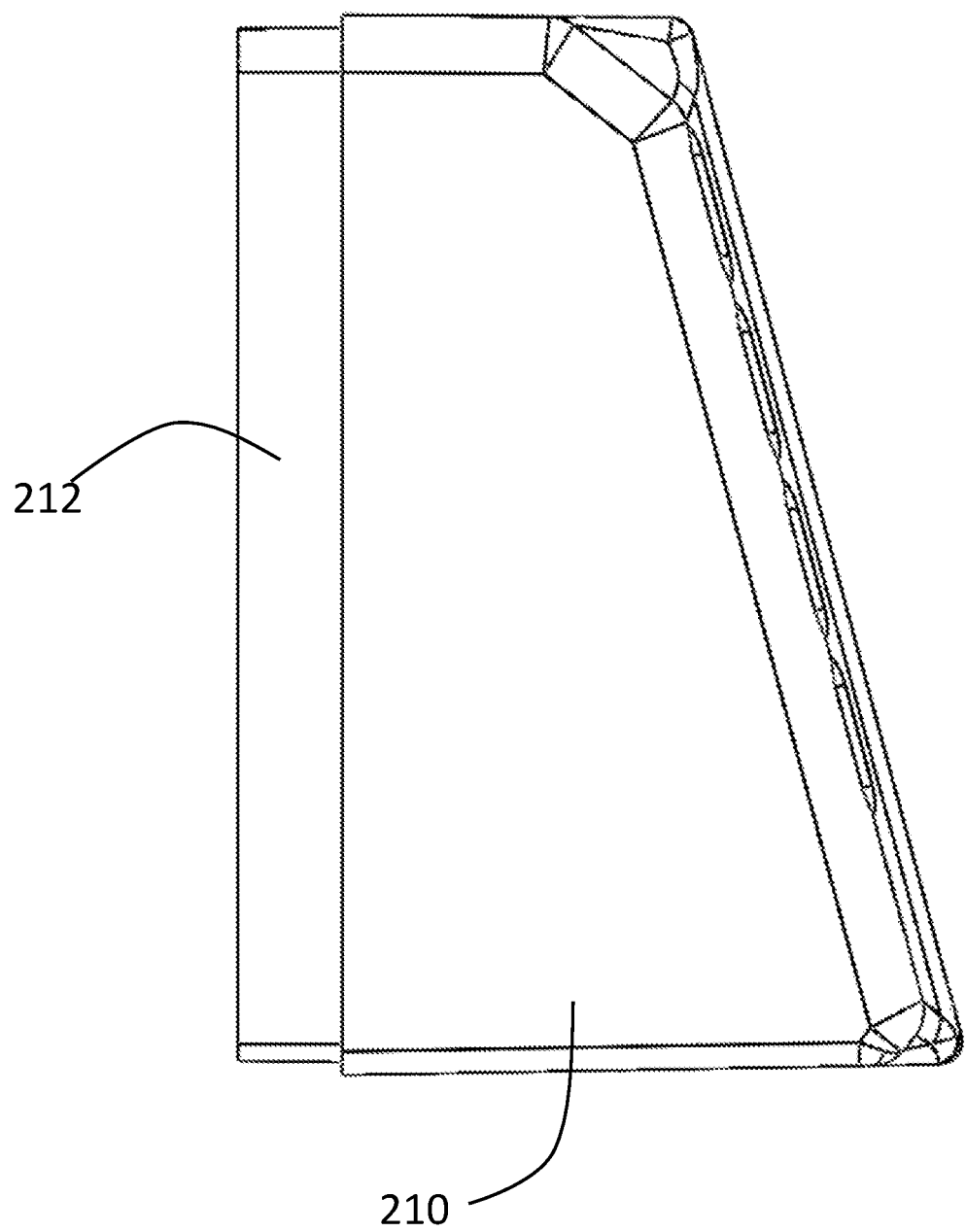
FIG. 2F is a left side view of an electrosurgical generator front panel frame in accordance with a preferred embodiment of the present invention.
Figure 2G:
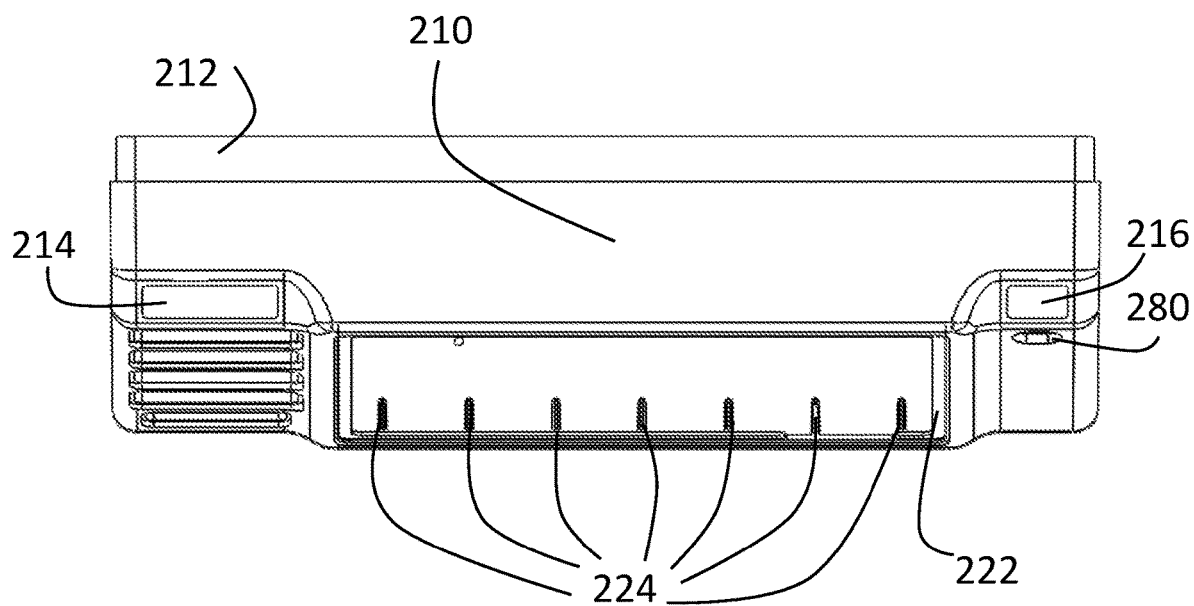
FIG. 2G is a top plan view of an electrosurgical generator front panel frame in accordance with a preferred embodiment of the present invention.
Figure 2H:
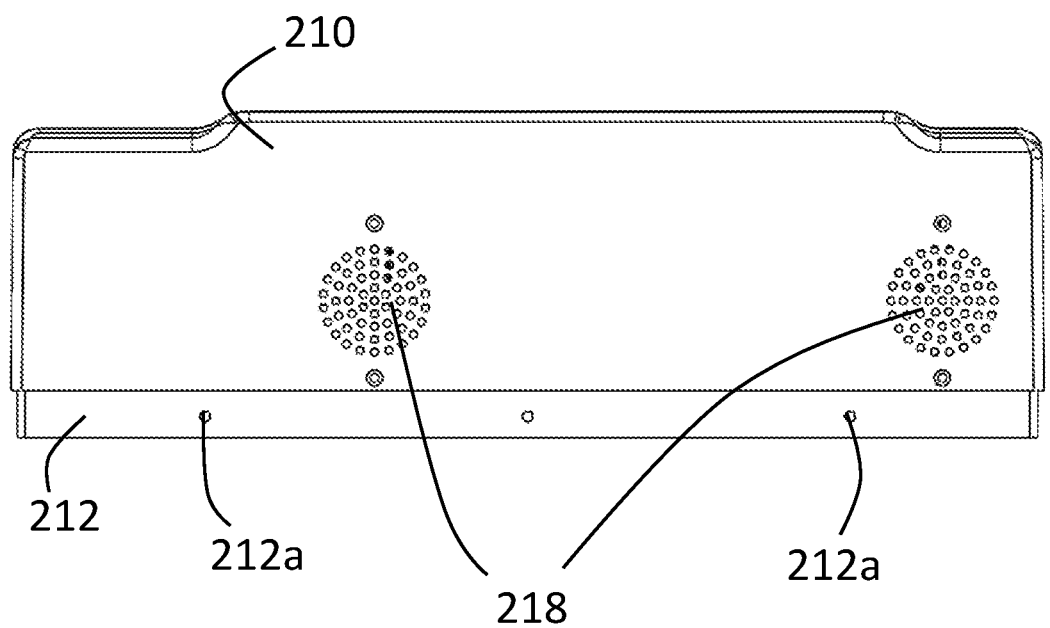
FIG. 2H is a bottom plan view of an electrosurgical generator front panel frame in accordance with a preferred embodiment of the present invention.

The preferred embodiments of the inventions are described with reference to the drawings. An electrosurgical or gas-enhanced electrosurgical generator has a housing having an interior compartment in which a plurality of modules or other gas or electrical elements are housed. Such other elements may include gas modules, a high frequency power module, a low frequency power module, an RFID reader, processors, or memory. The body of the housing has a base 110 with support structures 111 for mounting gas and/or power modules in the interior of the base and a plurality of vents 113, a pair of side support members 120, a rear panel 140, a shield panel 130, side rails 150 and a cover 160. The cover 160 may be connected to the back 140, for example, with screws through holes 162 in the cover and corresponding holes 142 in the back 140.

The housing further has front panel 200 has a body 210 has an opening 220 for receiving a display screen 390, for example a touchscreen display of a tablet computer, and a plurality of docks or openings 230, 240 for receiving various accessory plug modules for a gas-enhanced electrosurgical generator. The docks or openings 230, 240 each have at their rear one or more openings 232, 234, 242, 244 through which plug elements, such as a fluid or electrical connector, hose or wire 332*a*, can be connected to a module within the generator housing body. Further, for each opening 230, 240 there is an opening 234 for receiving a locking portion to hold the respective accessory plug module in place. The front panel further has an opening 280 for receiving an on/off button or switch 380 and a plurality of flat areas 214, 216 for receiving labels of identifying information. The front panel 200 may have one or more vents 218. Around the edge of the front panel 200 is a lip or flange 212 for mating with an edge of the generator body. The front panel 100 further has a lip or flange 222 around at least a portion of the opening 220 for holding the display in the opening and a plurality of support elements 224 for holding the display against the lip 222.

Further, on the back side of the front panel, there is a shield 250 to shield the accessory plug modules 230, 240 and wiring from the display and from a printed circuit board (PCB) or field-programmable gate array (FPGA) 350 mounted in a slot defined by openings 260. The front panel 200 also have a plurality holes 270 for receiving screws to connect the front panel 200 to the shield 130 and sides 120. The front panel similarly may have a plurality of holes 212*a* on the bottom side of the lip 212 to connect the front panel to the base 110.

Figure 3A:
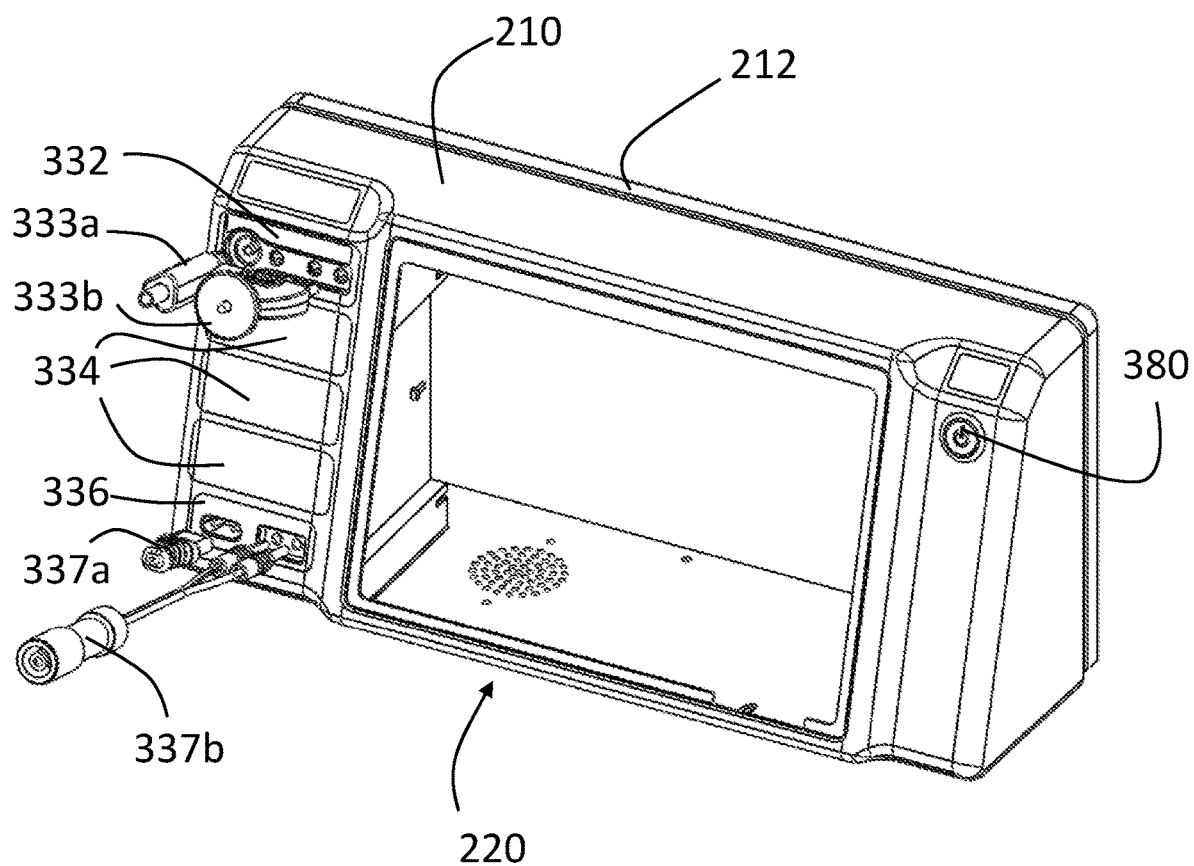
FIG. 3A is a front elevation view of an electrosurgical generator front panel assembly in accordance with a preferred embodiment of the present invention.
Figure 3B:
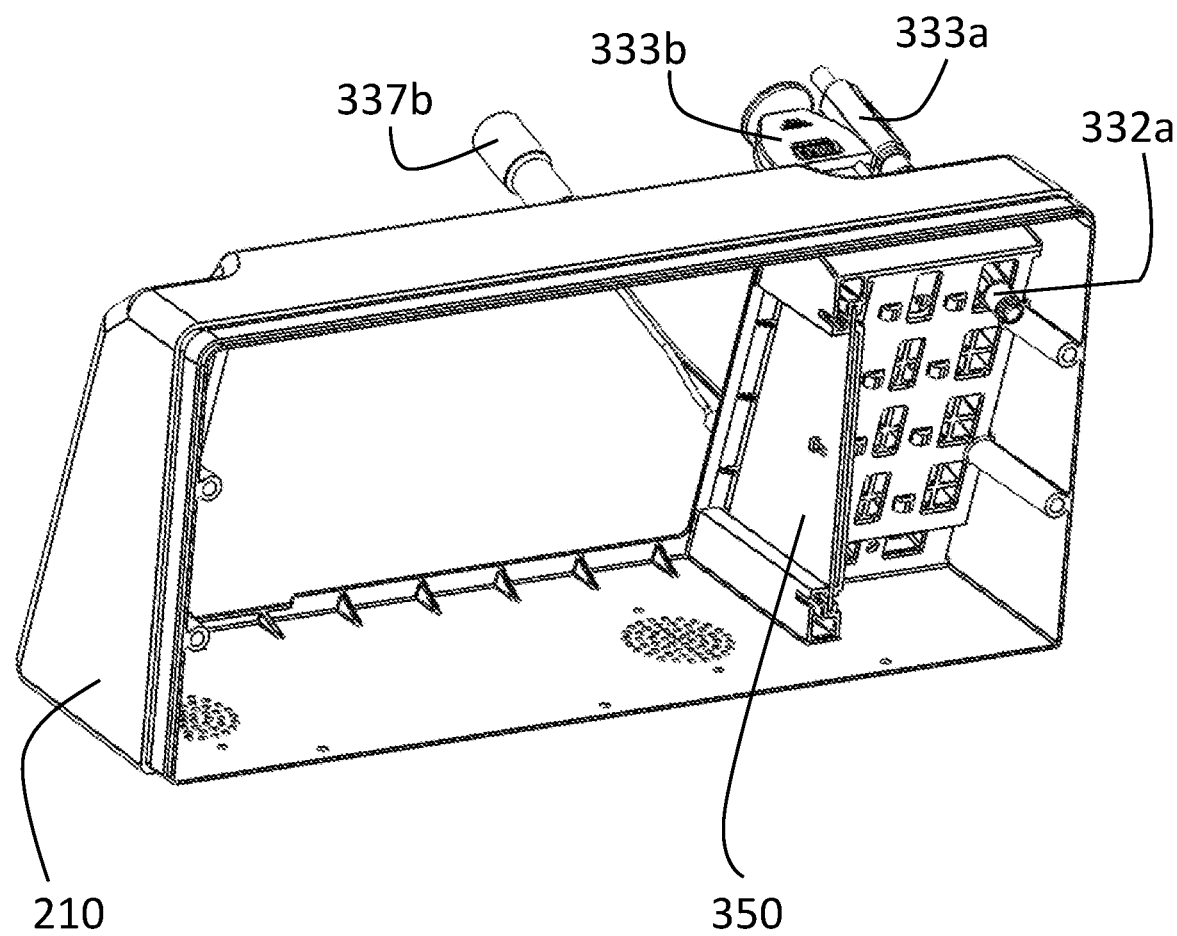
FIG. 3B is a rear elevation view of an electrosurgical generator front panel assembly in accordance with a preferred embodiment of the present invention.
Figure 3C:
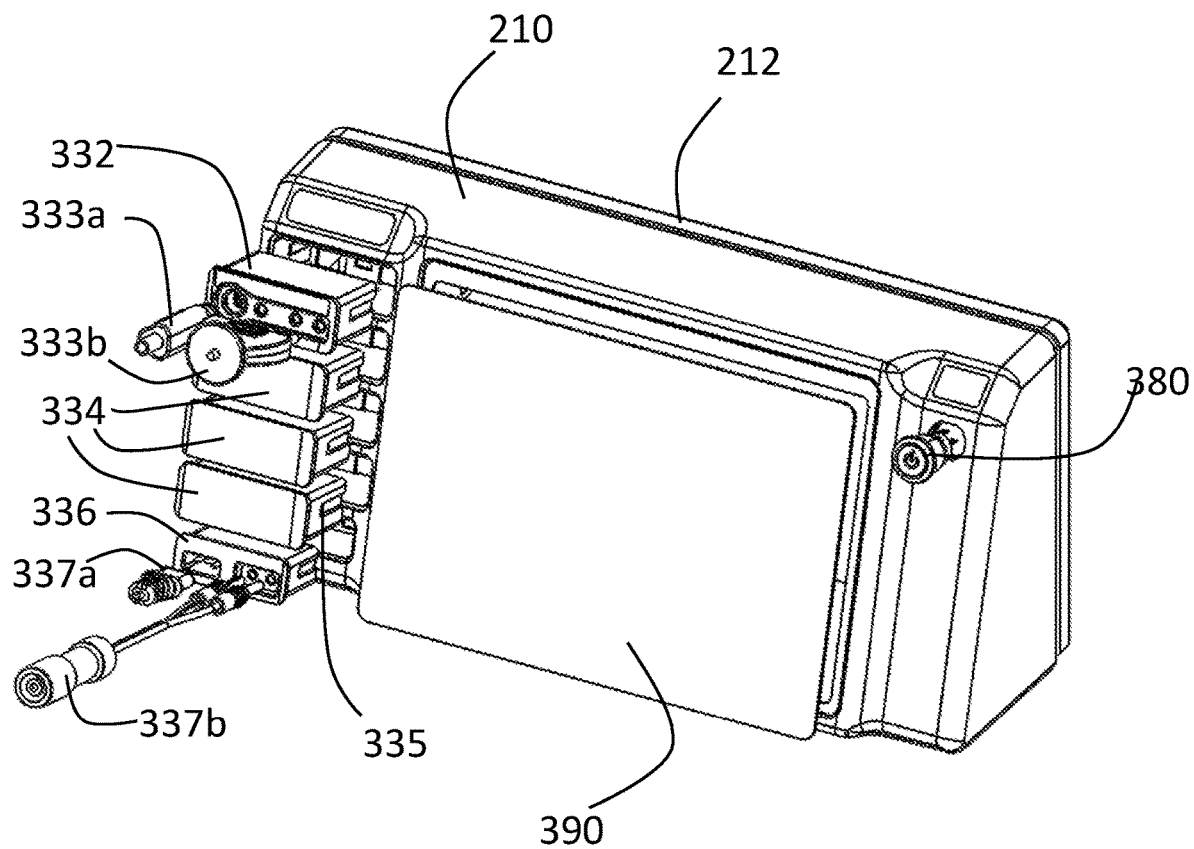
FIG. 3C is a front elevation view of an electrosurgical generator front panel assembly with a touchscreen display in accordance with a preferred embodiment of the present invention.

FIGS. 3A, 3B and 3C show a gas-enhanced electrosurgical generator front panel with a plurality of accessory plug modules 332, 337 and blank modules 334 in the openings 230. The accessory plug module 332 has a fluid connector 333*a* and a three-prong electrical connector 333*b*, that may be, for example, for an argon plasma, hybrid plasma or cold plasma accessory. Plug module 336 has a connector for power cords 337*a* and 337*b*. Each plug module may have, for example, an alignment or keying slot 335 on one or both sides for aligning with a corresponding ridge 231 in the front panel for inserting the plug module into the opening 230, 240.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A gas-enhanced electrosurgical generator housing comprising:
a configurable front panel comprising:
a body having a front face, a top, a bottom, a right and a left side, wherein said front face has an opening for receiving a touchscreen display, said opening for receiving a display being at an angle of less than 90 degrees relative to said bottom of said body;

a plurality of identical docks in said front face, each dock being configured to receive an accessory plug module, wherein each of said plurality of docks has an alignment feature on one interior side, wherein each of said plurality of docks has an opening located within said body for receiving a locking member of an accessory plug module;

a plug module in each of said docks in said front face, wherein each said plug module has an alignment feature on one outer side and a locking member.

2. A gas-enhanced electrosurgical generator housing according to claim 1, wherein at least one of said plug modules is a blank plug module having no connectors.

3. A gas-enhanced electrosurgical generator comprising:

a configurable front panel comprising:

a body having a front face, a top, a bottom, a right and a left side, wherein said front face has an opening for receiving a touchscreen display, said opening for receiving a touchscreen display being at an angle of less than 90 degrees relative to said bottom of said body;

a plurality of identically-shaped docks in said front face, each dock being configured to receive an accessory plug module, wherein each of said plurality of docks has an opening located within said body for receiving a locking portion of an accessory plug module;

a slot for receiving a printed circuit board; and a shield between said slot for receiving a printed circuit board and a said plurality of docks.

4. A gas-enhanced electrosurgical generator housing according to claim 3, further comprising:

a printed circuit board in said slot of receiving a printed circuit board.

\* \* \* \* \*